(12) United States Patent
Richard et al.

(10) Patent No.: US 10,959,697 B2
(45) Date of Patent: Mar. 30, 2021

(54) SYNCHRONIZATION FOR DYNAMIC IMAGING

(71) Applicant: CARESTREAM HEALTH, INC., Rochester, NY (US)

(72) Inventors: Samuel Richard, Rochester, NY (US); Xiaohui Wang, Pittsford, NY (US); Timothy J. Wojcik, Rochester, NY (US); Nathan J. Packard, Provo, UT (US)

(73) Assignee: Carestream Health, Inc., Rochester, NY (US)

( * ) Notice: Subject to any disclaimer, the term of this patent is extended or adjusted under 35 U.S.C. 154(b) by 27 days.

(21) Appl. No.: 16/344,846

(22) PCT Filed: Nov. 22, 2017

(86) PCT No.: PCT/US2017/062932
§ 371 (c)(1),
(2) Date: Apr. 25, 2019

(87) PCT Pub. No.: WO2018/098219
PCT Pub. Date: May 31, 2018

(65) Prior Publication Data
US 2020/0046310 A1    Feb. 13, 2020

Related U.S. Application Data

(60) Provisional application No. 62/425,648, filed on Nov. 23, 2016.

(51) Int. Cl.
*H05G 1/56* (2006.01)
*A61B 6/00* (2006.01)
*H04N 5/32* (2006.01)

(52) U.S. Cl.
CPC .............. *A61B 6/54* (2013.01); *A61B 6/4208* (2013.01); *A61B 6/482* (2013.01); *H04N 5/32* (2013.01)

(58) Field of Classification Search
CPC ......... A61B 6/54; A61B 6/025; A61B 6/4208; A61B 6/4233; A61B 6/482; A61B 6/5205;
(Continued)

(56) References Cited

U.S. PATENT DOCUMENTS 5,818,898 A    10/1998 Tsukamoto et al.
7,379,532 B2 *  5/2008 Kramp ................. A61B 6/4441
                                                    378/108
(Continued)

FOREIGN PATENT DOCUMENTS

EP    2 403 237 A1    1/2012
EP    2 614 772 A1    7/2013
WO    2016/094503 A1  6/2016

OTHER PUBLICATIONS

International Search Report dated Mar. 16, 2016 for International Application No. PCT/US2015/064683, 2 pages.
(Continued)

*Primary Examiner* — Irakli Kiknadze

(57) ABSTRACT

Synchronizing operation between a digital radiographic detector's integration periods and an x-ray generator's x-ray pulse rate by transmitting a frame rate to the detector and the generator. In a first mode, the detector monitors one or more pixels to detect an x-ray pulse. The firing time of the detected x-ray pulse relative to an internal clock of the detector is used to synchronize the detector's integration periods with the pulse rate of the x-ray generator based on the transmitted frame rate and the detected firing time of the
(Continued)

x-ray pulses. Successive pulses may also be used to determine a frame rate without prior transmission thereof.

19 Claims, 5 Drawing Sheets

(58) Field of Classification Search
CPC ... A61B 6/4283; A61B 6/4405; A61B 6/4411;
A61B 6/4423; A61B 6/4441; A61B
6/4452; A61B 6/487; A61B 6/545; A61B
6/548; A61B 6/56; A61B 6/032; A61B
6/541; A61B 6/585; A61B 6/481; A61B
6/504; A61B 6/00; A61B 6/488; A61B
6/4225; A61B 6/06; A61B 6/542; A61B
6/4241; A61B 6/4028; A61B 6/4042;
A61B 6/4488; A61B 6/563; A61B 6/027;
A61B 6/42; A61B 6/46; A61B 6/467;
A61B 6/586; H04N 5/32; H04N 5/353;
H04N 5/325; H04N 5/357; H04N 5/374;
H04N 5/781; H04N 7/18; H04N 5/23245;
H04N 5/361; H04N 5/378; H04L 5/0044;
H04L 5/006; G01T 1/247; G01T 1/16;
H01L 27/14643; G02B 27/01; H05G
1/60; G01N 23/04; G01N 2223/419;
G01N 23/046; G01N 23/044; G01N
23/083; G01N 2021/1765; G01N 21/25;
G01N 21/27; G01N 21/4795; G01N
21/6458; G01N 21/6486; G01N 33/4833;
G01N 23/20; G01N 2223/61

USPC .................................................. 378/114, 62
See application file for complete search history.

(56) References Cited

U.S. PATENT DOCUMENTS

| | | | |
|---|---|---|---|
| 9,035,265 B2 | 5/2015 | Yagi et al. | |
| 10,230,906 B2 | 3/2019 | Topfer et al. | |
| 2003/0083564 A1* | 5/2003 | Ghelmansarai | A61B 6/00 600/407 |
| 2009/0001276 A1* | 1/2009 | Yagi | A61B 6/032 250/370.09 |
| 2010/0046710 A1* | 2/2010 | Ohishi | A61B 6/481 378/106 |
| 2012/0201351 A1 | 8/2012 | Iwakiri et al. | |
| 2014/0061495 A1 | 3/2014 | Yagi et al. | |
| 2014/0110595 A1* | 4/2014 | Iwakiri | H04N 5/32 250/394 |
| 2016/0061966 A1 | 3/2016 | Kim et al. | |
| 2016/0106389 A1 | 4/2016 | Lim et al. | |
| 2017/0374295 A1 | 12/2017 | Topfer et al. | |

OTHER PUBLICATIONS

International Search Report dated Apr. 20, 2018 for International Application No. PCT/US2017/062932, 2 pages.

* cited by examiner

SYNCHRONIZATION FOR DYNAMIC IMAGING

CROSS REFERENCE TO RELATED APPLICATIONS

This application claims the benefit of and is a U.S. National Phase filing of PCT Application PCT/US2017/062932 filed Nov. 22, 2017 entitled "SYNCHRONIZATION FOR DYNAMIC IMAGING", in the name of Samuel Richard et al., which claims benefit of U.S. Patent Application Ser. No. 62/425,648, filed Nov. 23, 2016, in the name of Samuel Richard et al., and entitled SYNCHRONIZATION FOR BEDSIDE DYNAMIC IMAGING.

BACKGROUND OF THE INVENTION

The subject matter disclosed herein relates to fluoroscopy, cone beam computed tomography (CBCT), and tomosynthesis applications that require both high-frame rate data capture and synchronization between a digital radiographic detector and an x-ray generator. The synchronization allows the generator to fire while the detector is integrating (integration window). Often this is accomplished with a hardware tether between the detector and generator. It is desired to operate the detector and generator wirelessly for use in bedside applications.

Traditionally, wireless captures occur by triggering the detector to start integrating. However this introduces timing uncertainty between the generator's exposure period and the detector's integration period. The uncertainty is caused by uncontrollable elements, such as delays between the detector and operating system and transmission delays. To compensate, the integration window is set to a longer time than the x-ray pulse width. A large integration window reduces the maximum frame rate, and can limit the functionality of fluoroscopy and tomosynthesis applications.

With bedside dynamic imaging applications, such as fluoroscopy and tomosynthesis, it is important to keep the frame's integration window small while ensuring the generator fires only during the integration window. The discussion above is merely provided for general background information and is not intended to be used as an aid in determining the scope of the claimed subject matter.

BRIEF DESCRIPTION OF THE INVENTION

It is desirable to synchronize the detector and generator such that the generator's periodic x-ray pulse always falls within the detector's integration window. Further, it is desirable to minimize the latency between the user initiating the acquisition and the generator firing.

Synchronizing operation between a digital radiographic detector's integration periods and an x-ray generator's x-ray pulse rate by transmitting a frame rate to the detector and the generator is disclosed. In a first mode, the detector monitors one or more pixels to detect an x-ray pulse. The firing time of the detected x-ray pulse relative to an internal clock of the detector is used to synchronize the detector's integration periods with the pulse rate of the x-ray generator based on the transmitted frame rate and the detected firing time of the x-ray pulses. Successive pulses may also be used to determine a frame rate without prior transmission thereof.

In one embodiment, a method that synchronizes operation between a digital radiographic detector's integration periods and an x-ray generator's x-ray pulse rate first communicates a frame rate to the detector and the generator. The detector then operates in a first mode by reading out one or more frames from the detector row by row continuously. The detector monitors each read out row of pixels to detect a high output which indicates that the x-ray generator has fired an x-ray pulse that impacted the detector. A start time of the generator emitting the detected x-ray pulse can be determined by the detector relative to an internal clock of the detector using a known row read out time interval corresponding to the detector and a row number of the row being read out when the x-ray pulse reached the detector. The detector may then be operated in a second mode wherein its integration periods are synchronized with start times of the generator emitting x-ray pulses based on the communicated frame rate and the determined start time of the detected x-ray pulse.

In another embodiment, a method that synchronizes operation between a digital radiographic detector's integration periods and an x-ray generator's x-ray pulse rate first communicates a frame rate to the detector and the generator. The detector then operates in a first mode by monitoring one or more pixels in the detector to detect an x-ray pulse from the x-ray generator. A start time of the generator emitting the detected x-ray pulse can be determined by the detector using an internal clock of the detector. The detector may then be operated in a second mode wherein its integration periods are synchronized with start times of the generator emitting x-ray pulses based on the communicated frame rate and the determined start time of the detected x-ray pulse.

In another embodiment, a method that synchronizes operation between a digital radiographic detector's integration periods and an x-ray generator's x-ray pulse rate monitors one or more pixels in the detector to detect an x-ray pulse from the x-ray generator. A start time of the generator emitting the detected x-ray pulse can be determined by the detector using an internal clock of the detector. A second pulse from the x-ray generator is detected and the time between pulses is used to determine the x-ray generator's pulse rate. The detector may then be operated in a second mode wherein its integration periods are synchronized with pulse rate of the generator.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

This application claims priority to U.S. Patent Application Ser. No. 62/425,648, filed Nov. 23, 2016, in the name of Richard et al., and entitled SYNCHRONIZATION FOR BEDSIDE DYNAMIC IMAGING, which is hereby incorporated by reference herein in its entirety.

This application is related in certain respects to U.S. Patent Application PCT/US2015/064683, having International Filing Date Dec. 9, 2015, in the name of Topfer et al., and entitled BEAM DETECTION WITH CONTINUOUS DETECTOR READOUT which is hereby incorporated by reference herein in its entirety.

Figure 1:
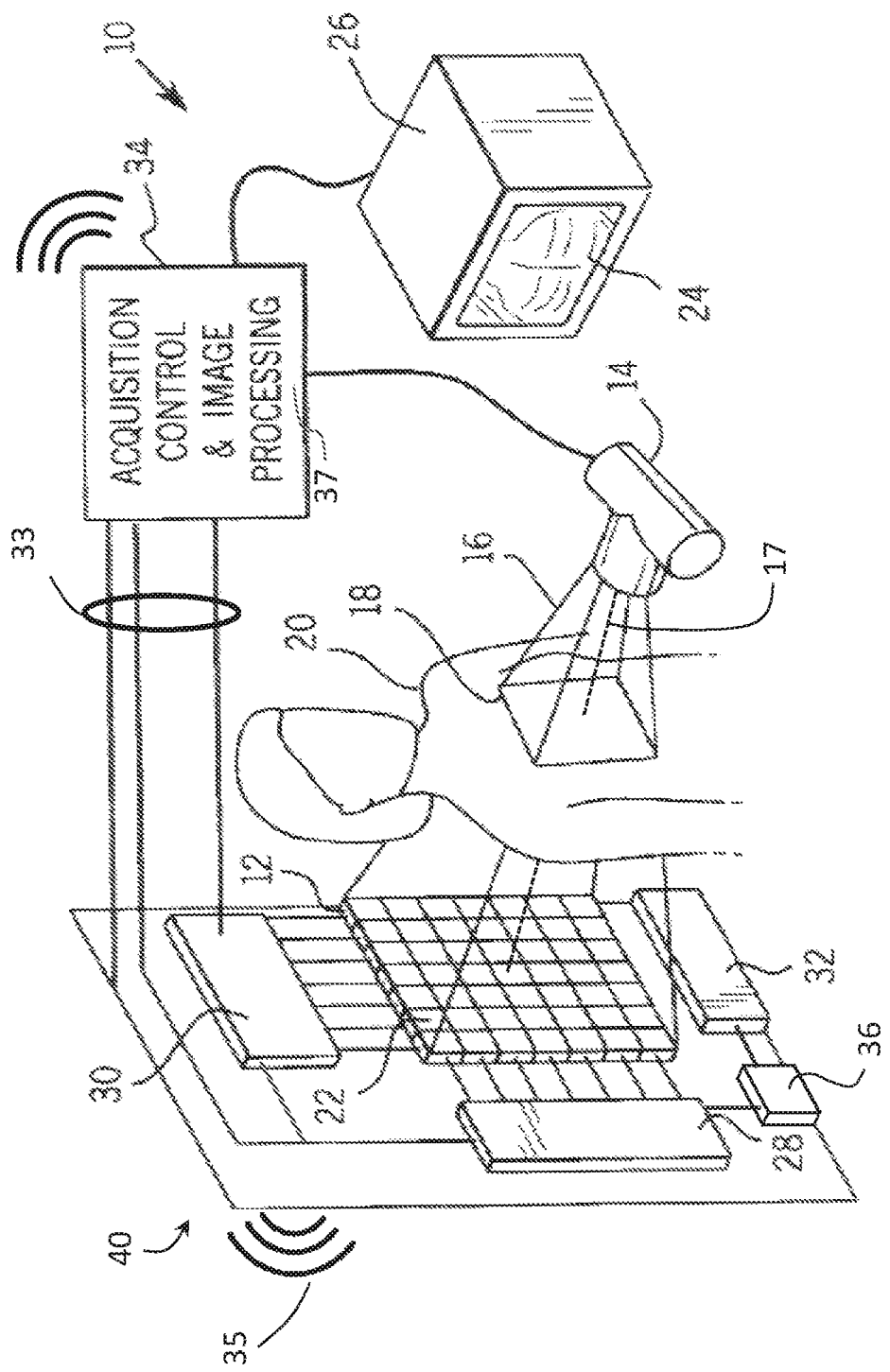
FIG. 1 is a schematic perspective view of an exemplary x-ray imaging system.

FIG. 1 is a perspective view of a digital radiographic (DR) imaging system 10 that may include a generally curved or planar DR detector 40 (shown in a planar embodiment and without a housing for clarity of description), an x-ray generator (or x-ray source) 14 configured to generate radiographic energy (x-ray radiation), and a digital monitor, or electronic display, 26 configured to display images captured by the DR detector 40, according to one embodiment. The DR detector 40 may include a two dimensional array 12 of detector cells, or photosensors, 22 arranged in electronically addressable rows and columns. These photosensors 22 may be referred to herein as imaging pixels or detector pixels. The DR detector 40 may be positioned to receive x-rays 16 passing through a subject 20 during a radiographic energy exposure, or radiographic energy pulse, emitted by the x-ray source 14. As shown in FIG. 1, the radiographic imaging system 10 may use an x-ray source 14 that emits collimated x-rays 16, e.g. an x-ray beam, selectively aimed at and passing through a preselected region 18 of the subject 20. The x-ray beam 16 may be attenuated by varying degrees along its plurality of rays according to the internal structure of the subject 20, which attenuated rays are detected by the array 12 of photosensitive detector cells 22. The curved or planar DR detector 40 is positioned, as much as possible, in a perpendicular relation to a substantially central ray 17 of the plurality of rays 16 emitted by the x-ray source 14. In a curved array embodiment, the source 14 may be centrally positioned such that a larger percentage, or all, of the photosensitive detector cells are positioned perpendicular to incoming x-rays from the centrally positioned source 14. The array 12 of individual photosensitive cells (pixels) 22 may be electronically addressed (scanned) by their position according to column and row. As used herein, the terms "column" and "row" refer to the vertical and horizontal arrangement of the photosensor cells 22 and, for clarity of description, it will be assumed that the rows extend horizontally and the columns extend vertically. However, the orientation of the columns and rows is arbitrary and does not limit the scope of any embodiments disclosed herein. Furthermore, the term "subject" may be illustrated as a human patient in the description of FIG. 1. however, a subject of a DR imaging system, as the term is used herein, may be a human, an animal, an inanimate object, or a portion thereof.

In one exemplary embodiment, the rows of photosensitive cells 22 may be scanned one or more at a time by electronic scanning circuit 28 so that the exposure data from the array 12 may be transmitted to electronic read-out circuit 30. Each photosensitive cell 22 may independently detect and store a charge proportional to an intensity, or energy level, of the attenuated radiographic radiation, or x-rays, received and absorbed in the cell. Thus, each photosensitive cell, when read-out, provides detected information defining a pixel of a radiographic image 24, e.g. a brightness level or an amount of energy absorbed by the pixel, that may be digitally decoded by image processing electronics 34 and transmitted to be displayed by the digital monitor 26 for viewing by a user. If no stored charge is detected during read out of a photosensitive cell, it may be concluded by the read out circuitry that the x-ray generator has not fired an x-ray pulse. If a stored charge above a preset voltage threshold is detected during read out of a photosensitive cell, it may be concluded by the read out circuitry that the x-ray generator has fired an x-ray pulse that is detected by the particular photosensitive cell being read out. An internal clock in the detector, either a dedicated timer (not shown) or a programmed clock circuit, may be used to store a time when the x-ray pulse is detected. An electronic bias circuit 32 is electrically connected to the two-dimensional detector array 12 to provide a bias voltage to each of the photosensitive cells 22.

Each of the bias circuit 32, the scanning circuit 28, and the read-out circuit 30, may communicate with an acquisition control and image processing unit 34 over a connected cable 33 (wired), or the DR detector 40 and the acquisition control and image processing unit 34 may be equipped with a wireless transmitter and receiver to transmit radiographic image data wirelessly 35 to the acquisition control and image processing unit 34. The acquisition control and image processing unit 34 may include a processor and electronic memory (not shown) to control operations of the DR detector 40 as described herein, including control of circuits 28, 30, and 32, for example, by use of programmed instructions. and to store and process image data. The acquisition control and image processing unit 34 may also be used to control activation of the x-ray source 14 over a hardwire connection 37 during a radiographic exposure, controlling an x-ray tube electric current magnitude, and thus the fluence of x-rays in x-ray beam 16, and/or the x-ray tube voltage, and thus the energy level of the x-rays in x-ray beam 16. A portion or all of the acquisition control and image processing unit 34 functions may reside in the detector 40 in an on-board processing system 36 which may include a processor and electronic memory to control operations of the DR detector 40 as described herein, including control and timing of circuits 28, 30, and 32, such as synchronizing an integration window as described herein by use of programmed instructions, and to store and process image data similar to the functions of standalone acquisition control and image processing system 34. The image processing system may perform image integration and image disposition functions as described herein. The image processing system 36 may control image transmission, image processing, and image correction on board the detector 40 based on instructions or other commands transmitted from the acquisition control and image processing unit 34, and transmit corrected digital image data therefrom. Alternatively, acquisition control and image processing unit 34 may receive raw image data from the detector 40 and process the image data and store it, or it may store raw unprocessed image data in local memory, or in remotely accessible memory.

With regard to a direct detection embodiment of DR detector 40, the photosensitive cells 22 may each include a sensing element sensitive to x-rays, i.e. it absorbs x-rays and generates an amount of charge carriers in proportion to a magnitude of the absorbed x-ray energy. A switching element may be configured to be selectively activated to read out the charge level of a corresponding x-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, may be disposed over the light sensitive sensing elements to convert incident x-ray radiographic energy to visible light energy. Thus, in the embodiments disclosed herein, it should be noted that the DR detector 40 (or DR detector 300 in FIG. 3 or DR detector 400 in FIG. 4) may include an indirect or direct type of DR detector.

Examples of sensing elements used in sensing array 12 include various types of photoelectric conversion devices (e.g., photosensors) such as photodiodes (P-N or PIN diodes), photo-capacitors (MIS), photo-transistors or photo-conductors. Examples of switching elements used for signal read-out include a-Si TFTs, oxide TFTs, MOS transistors, bipolar transistors and other p-n junction components.

Figure 2:
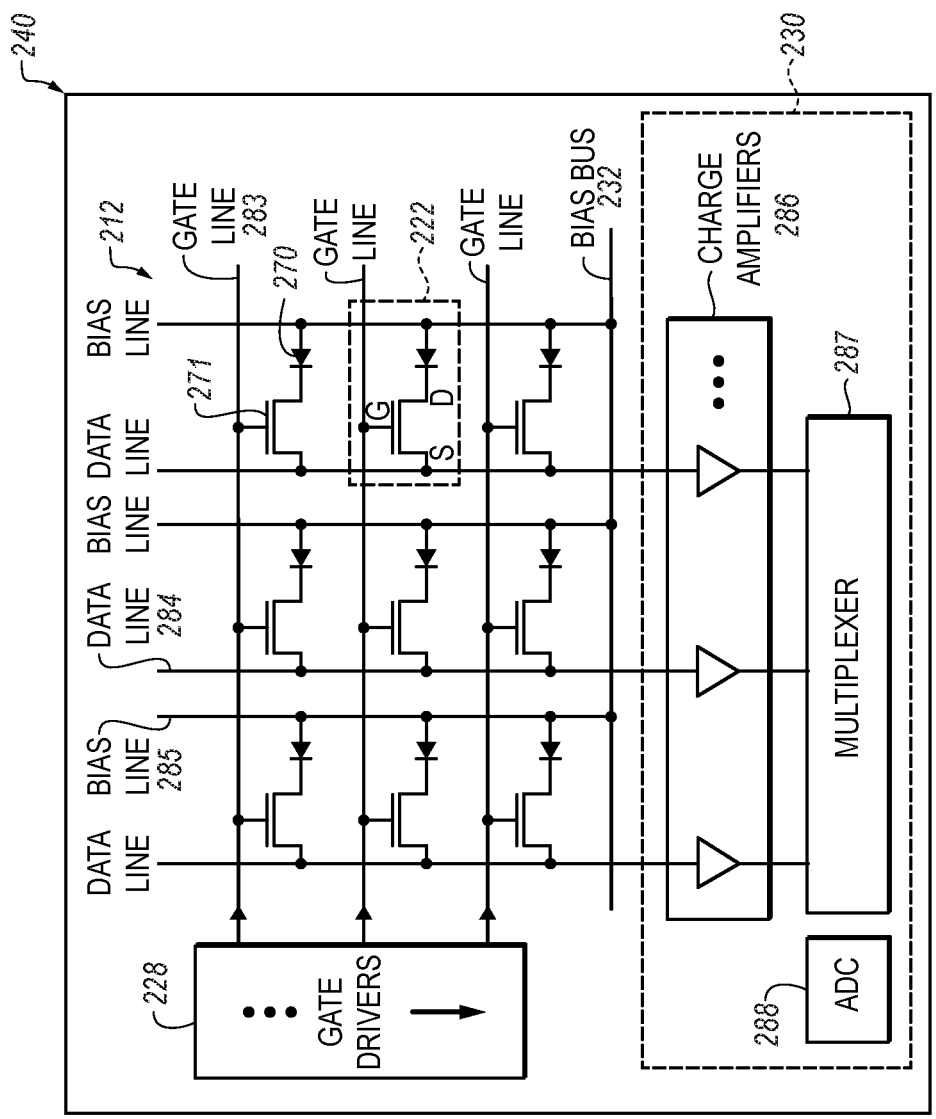
FIG. 2 is a schematic diagram of a photosensor array in a radiographic detector.

FIG. 2 is a schematic diagram 240 of a portion of a two-dimensional array 12 for a DR detector 40. The array of photosensor cells 212, whose operation may be consistent with the photosensor array 12 described above, may include a number of hydrogenated amorphous silicon (a-Si:H) n-i-p photodiodes 270 and thin film transistors (TFTs) 271 formed as field effect transistors (FETs) each having gate (G), source (S), and drain (D) terminals. In embodiments of DR detector 40 disclosed herein, such as a multilayer DR detector (400 of FIG. 4), the two-dimensional array of photosensor cells 12 may be formed in a device layer that abuts adjacent layers of the DR detector structure, which adjacent layers may include a rigid glass layer or a flexible polyimide layer or a layer including carbon fiber without any adjacent rigid layers. A plurality of gate driver circuits 228 may be electrically connected to a plurality of gate lines 283 which control a voltage applied to the gates of TFTs 271, a plurality of readout circuits 230 may be electrically connected to data lines 284, and a plurality of bias lines 285 may be electrically connected to a bias line bus or a variable bias reference voltage line 232 which controls a voltage applied to the photodiodes 270. Charge amplifiers 286 may be electrically connected to the data lines 284 to receive signals therefrom. Outputs from the charge amplifiers 286 may be electrically connected to a multiplexer 287, such as an analog multiplexer, then to an analog-to-digital converter (ADC) 288, or they may be directly connected to the ADC, to stream out the digital radiographic image data at desired rates. In one embodiment, the schematic diagram of FIG. 2 may represent a portion of a DR detector 40 such as an a-Si:H based indirect flat panel, curved panel, or flexible panel imager.

Incident x-rays, or x-ray photons, 16 are converted to optical photons, or light rays, by a scintillator, which light rays are subsequently converted to electron-hole pairs, or charges, upon impacting the a-Si:H n-i-p photodiodes 270. In one embodiment, an exemplary detector cell 222, which may be equivalently referred to herein as a pixel, may include a photodiode 270 having its anode electrically connected to a bias line 285 and its cathode electrically connected to the drain (D) of TFT 271. The bias reference voltage line 232 can control a bias voltage of the photodiodes 270 at each of the detector cells 222. The charge capacity of each of the photodiodes 270 is a function of its bias voltage and its capacitance. In general, a reverse bias voltage, e.g. a negative voltage, may be applied to the bias lines 285 to create an electric field (and hence a depletion region) across the pn junction of each of the photodiodes 270 to enhance its collection efficiency for the charges generated by incident light rays. Referred to herein as an integration period, or integration phase, the image signal represented by the array of photosensor cells 212 may be integrated, or captured, by the photodiodes while their associated TFTs 271 are held in a non-conducting (off) state, for example, by maintaining the gate lines 283 at a negative voltage via the gate driver circuits 228. The photosensor cell array 212 may then be read out by sequentially switching rows of the TFTs 271 to a conducting (on) state by means of the gate driver circuits 228. When a row of the pixels 22 is switched to a conducting state, for example by applying a positive voltage to the corresponding gate line 283, collected charge from the photodiode in those pixels may be transferred along data lines 284 to the external charge amplifier circuits 286. The row may then be switched back to a non-conducting state, and the process is repeated for each row until the entire array of photosensor cells 212 has been read out. The integrated signal outputs are transferred from the external charge amplifiers 286 to an analog-to-digital converter (ADC) 288 using a parallel-to-serial converter, such as multiplexer 287, which together comprise read-out circuit 230. As described herein, the signal outputs, e.g., a voltage level, for each row or for each pixel 22 may be measured to detect whether x-ray energy has reached the detector, indicating whether or not the x-ray source 14 has been fired.

This digital image information may be subsequently processed by image processing system 34 to yield a digital image which may then be digitally stored and immediately displayed on monitor 26, or it may be displayed at a later time by accessing the digital electronic memory containing the stored image. The flat panel DR detector 40 and the x-ray source 14 may be capable of both single-shot (e.g., static radiographic) and continuous image acquisition such as for fluoroscopy, CBCT, and tomosynthesis applications, which may require transmitted frame rates of about 30 frames per second, 60 frames per second, or more.

Figure 3:
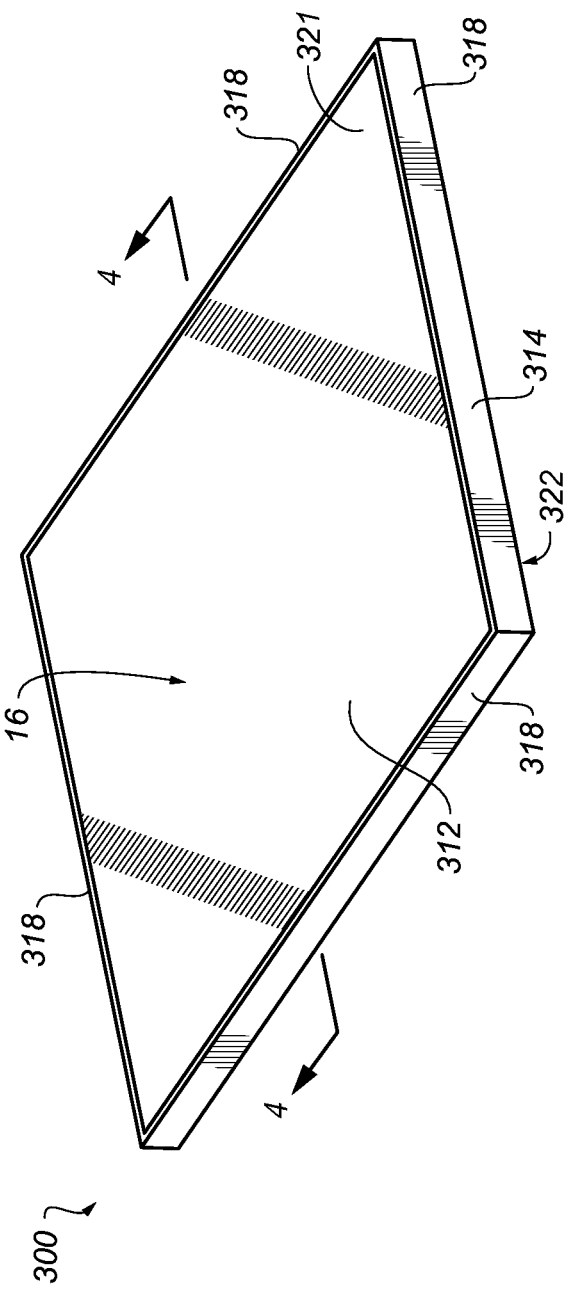
FIG. 3 is a diagram of a DR detector.

FIG. 3 shows a perspective view of an exemplary prior art generally rectangular, planar, portable wireless DR detector 300 according to an embodiment of DR detector 40 disclosed herein. The DR detector 300 may include a flexible substrate to allow the DR detector to capture radiographic images in a curved orientation. The flexible substrate may be fabricated in a permanent curved orientation, or it may remain flexible throughout its life to provide an adjustable curvature in two or three dimensions, as desired. The DR detector 300 may include a similarly flexible housing portion 314 that surrounds a multilayer structure comprising a flexible photosensor array portion 22 of the DR detector 300. The housing portion 314 of the DR detector 300 may include a continuous, rigid or flexible, x-ray opaque material or, as used synonymously herein a radiopaque material, surrounding an interior volume of the DR detector 300. The housing portion 314 may include four flexible edges 318, extending between the top side 321 and the bottom side 322, and arranged substantially orthogonally in relation to the top and bottom sides 321, 322. The bottom side 322 may be continuous with the four edges and disposed opposite the top side 321 of the DR detector 300. The top side 321 comprises a top cover 312 attached to the housing portion 314 which, together with the housing portion 314, substantially encloses the multilayer structure in the interior volume of the DR detector 300. The top cover 312 may be attached to the housing 314 to form a seal therebetween, and be made of a material that passes x-rays 16 without significant attenuation thereof, i.e., an x-ray transmissive material or, as used synonymously herein, a radiolucent material, such as a carbon fiber plastic, polymeric, or other plastic based material.

Figure 4:
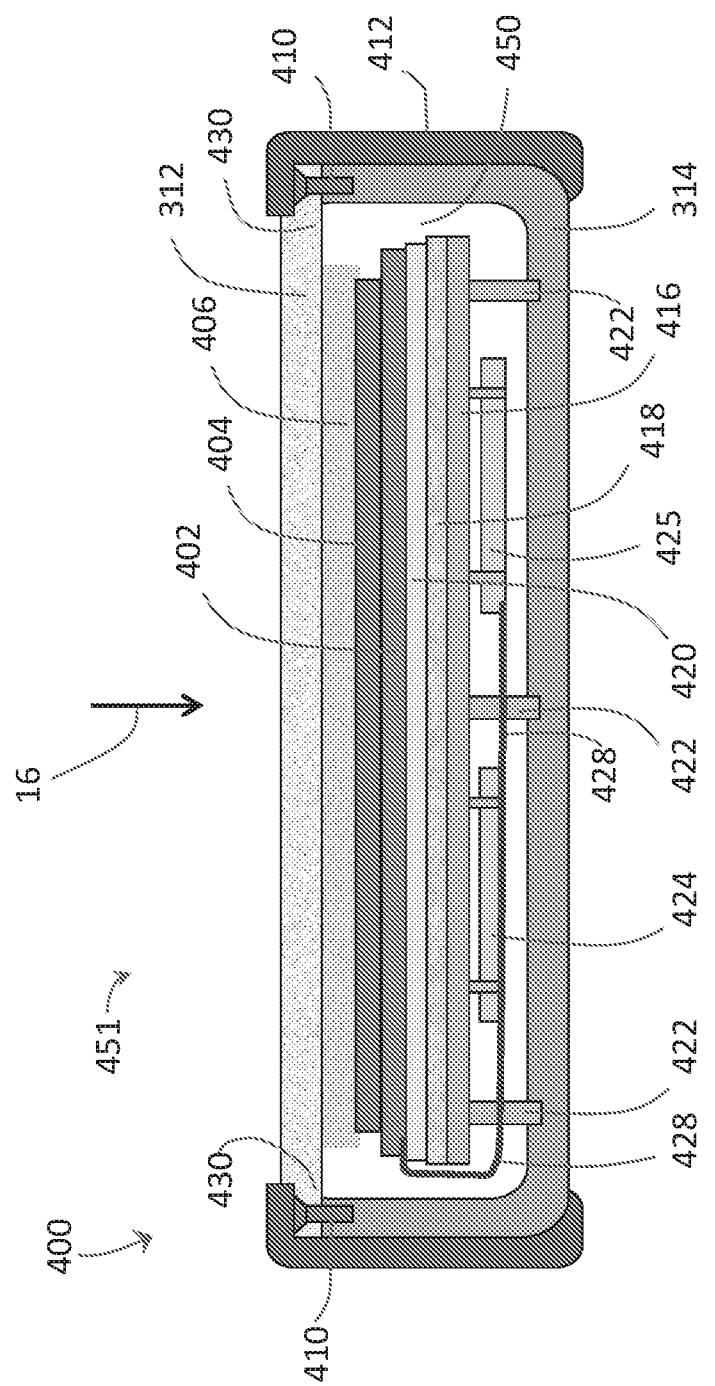
FIG. 4 is a cross section diagram of an exemplary DR detector.

With reference to FIG. 4, there is illustrated in schematic form an exemplary cross-section view along section 4-4 of the exemplary embodiment of the DR detector 300 (FIG. 3). For spatial reference purposes, one major surface of the DR detector 400 may be referred to as the top side 451 and a second major surface may be referred to as the bottom side 452, as used herein. The multilayer structure may be disposed within the interior volume 450 enclosed by the housing 314 and top cover 312 and may include a flexible curved or planar scintillator layer 404 over a curved or planar the two-dimensional imaging sensor array 12 shown schematically as the device layer 402. The scintillator layer 404 may be directly under (e.g., directly connected to) the substantially planar top cover 312, and the imaging array 402 may be directly under the scintillator 404. Alternatively, a flexible layer 406 may be positioned between the scintillator layer 404 and the top cover 312 as part of the multilayer structure to allow adjustable curvature of the multilayer structure and/or to provide shock absorption. The flexible layer 406 may be selected to provide an amount of flexible support for both the top cover 312 and the scintillator 404, and may comprise a foam rubber type of material. The layers just described comprising the multilayer structure each may generally be formed in a rectangular shape and defined by edges arranged orthogonally and disposed in parallel with an interior side of the edges 318 of the housing 314, as described in reference to FIG. 3.

A substrate layer 420 may be disposed under the imaging array 402, such as a rigid glass layer, in one embodiment, or flexible substrate comprising polyimide or carbon fiber upon which the array of photosensors 402 may be formed to allow adjustable curvature of the array, and may comprise another layer of the multilayer structure. Under the substrate layer 420 a radiopaque shield layer 418 may be used as an x-ray blocking layer to help prevent scattering of x-rays passing through the substrate layer 420 as well as to block x-rays reflected from other surfaces in the interior volume 450. Readout electronics, including the scanning circuit 28, the read-out circuit 30, the bias circuit 32, and processing system 36 (all of FIG. 1) may be formed adjacent the imaging array 402 or, as shown, may be disposed below frame support member 416 in the form of integrated circuits (ICs) electrically connected to printed circuit boards 424, 425. The imaging array 402 may be electrically connected to the readout electronics 424 (ICs) over a flexible connector 428 which may comprise a plurality of flexible, sealed conductors known as chip-on-film (COF) connectors.

X-ray flux may pass through the radiolucent top panel cover 312, in the direction represented by an exemplary x-ray beam 16, and impinge upon scintillator 404 where stimulation by the high-energy x-rays 16, or photons, causes the scintillator 404 to emit lower energy photons as visible light rays which are then received in the photosensors of imaging array 402. The frame support member 416 may connect the multilayer structure to the housing 314 and may further operate as a shock absorber by disposing elastic pads (not shown) between the frame support beams 422 and the housing 314. Fasteners 410 may be used to attach the top cover 312 to the housing 314 and create a seal therebetween in the region 430 where they come into contact. In one embodiment, an external bumper 412 may be attached along the edges 318 of the DR detector 400 to provide additional shock-absorption.

Figure 5:
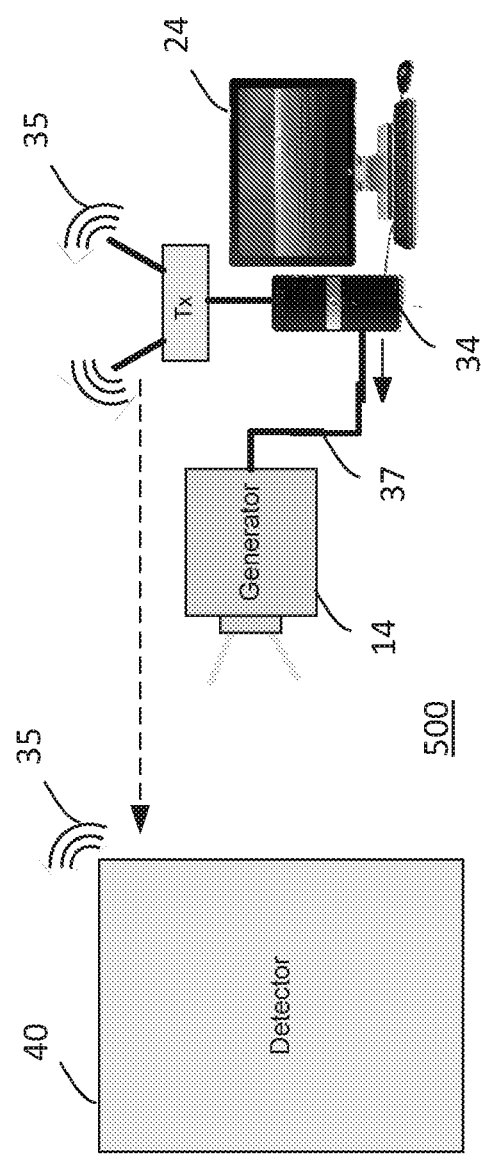
FIG. 5 is a another perspective view of an exemplary x-ray imaging system.

FIG. 5 is a diagram showing an x-ray system 500 including components similar in operation as described herein in relation to the x-ray imaging system 10 of FIG. 1. As described herein the components of x-ray system 500 are illustrated for ease of description, however, those skilled in the art will recognize that the x-ray generator 14 and the detector 40 may be configured to operate in radiographic imaging modes including fluoroscopy, CBCT, and tomosynthesis applications. In one embodiment, the integration periods of the digital radiographic detector 40 and the pulse rate of the x-ray generator 14 may be synchronized to enable fluoroscopic imaging, which images may be wirelessly 35 transmitted by the detector 40, at frame rates between about 30 frames per second and 60 frames per second, to the image processing control 34 for live video display on a monitor 24. In one mode of operation, the image processing control 34 communicates a frame rate, i.e., time between pulses in milliseconds or microseconds, wirelessly 35 to the detector 40 and over a hard wire communication channel 37 to the x-ray generator 14. The detector may be programmed to operating in a first mode at this time, which may be referred to as a standby mode, by continuously reading out one or more data frames from the detector row by row continuously. An operator of the x-ray system may selectively activate the standby mode using known input means for the image processing control 34.

As the term data frame is used herein, a data frame contains the data as stored in all of the pixels of detector 40, which data frames, or frames, may contain dark image data wherein the x-ray source is not activated during an integration period of the detector 40. Dark images may be used for calibration purposes by the detector 40. The data frame may contain flash data wherein the x-ray source is activated so that the entire detector array is exposed to the x-ray beam in order to perform diagnostic tests and calibration of the pixels and read out circuitry. The data frames may also contain image data captured during examination procedures of patients or other subjects.

During the row by row readout, the detector monitors each read out row of pixels to detect during which row being read out an x-ray pulse from the x-ray generator reaches the detector. This is indicated by an amount of charge captured in a pixel or row of pixels above a preset threshold, as measured and detected by the read out circuitry, typically as a voltage level. In one embodiment, for faster detection of an x-ray pulse, selected ones of the detector's pixels may be monitored during this first standby mode of operation. A subset of the pixels may be addressed for monitoring so that the selected subset of pixels may be scanned in a shorter amount of time as compared to scanning the entire array row by row. When an x-ray pulse is detected during the first mode of operation, the time of the detection is noted by the detector, such as by storing the time in electronic memory, in relation to an internal clock of the detector. The x-ray pulse start time may also be calculated using a known row read out time interval corresponding to the detector and a row number of the row containing the pixel whose detected signal indicates that the x-ray generator is activated. The x-ray generator start time may thus be stored in the detector in relation to an internal clock, in relation to a row being read out when the x-ray pulse reached the detector, or in a time phase, or time difference, relationship relative to a time for reading a particular row of the detector, such as the first (top) row or the last (bottom) row of the detector's pixels. Because the detector 40 is programmed to store the previously transmitted frame rate, the detector 40 may calculate the start time of the next x-ray generator pulse based on the determined start time of the previous x-ray pulse. When the next x-ray generator pulse start time is determined, the detector may transition to a second synchronization mode by selectively adjusting its integration periods to synchronize with the expected calculated start times of the generator emitting x-ray pulses.

Figure 6:
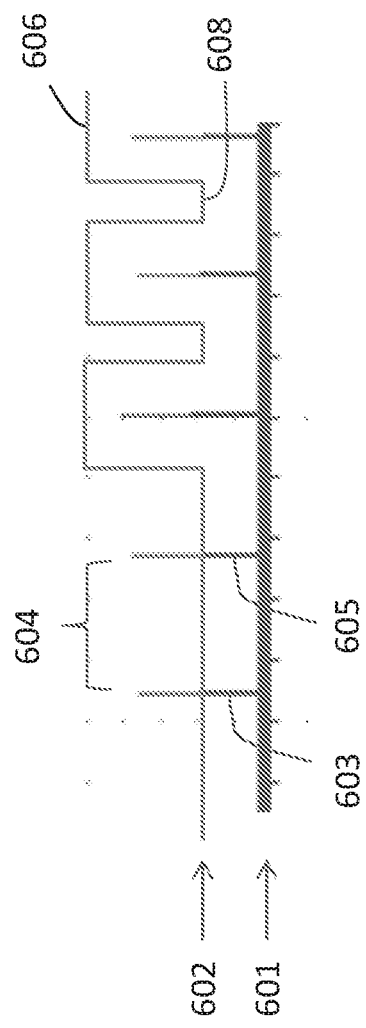
FIG. 6 illustrates an example diagram of timed x-ray generator pulses and detector integration periods.

The synchronized integration periods may be explained in relation to the timing diagram of FIG. 6, which illustrates an x-ray generator pulse time line 601 showing five exemplary x-ray beam pulses wherein x-ray pulses 603, 605, may be referred to herein as first and second x-ray pulses. The frame rate of the x-ray pulses 603, 605, may be defined as the time between pulses 605, which may be communicated in units of microseconds or milliseconds. The exemplary detector time line 602 illustrates integration periods 606, corresponding to a detector time line "high", and read out periods 608, corresponding to a detector time line "low". The integration periods 606 synchronized with the x-ray generator pulses illustrate a preferred timing embodiment whereby the integration period is programmed to start before the x-ray generator is activated to emit an x-ray pulse and is programmed to end after the x-ray pulse is terminated, whereafter the detector array image frame read out 608 takes place. Although the first integration period 606 illustrated in FIG. 6 is shown to take place after the second x-ray pulse 605, the first integration period may be programmed to capture an image data frame exposed by the second x-ray pulse 605. The FIG. 6 timing diagram as shown illustrates one embodiment of the present invention disclosed herein, wherein the frame rate is not transmitted by the image processing system 34.

In one embodiment, a special individual photosensor 222 in the photosensor array 240 of the detector may be fabricated to be read out at rate at least about ten times the row read out rate of the detector to detect when an x-ray pulse from the x-ray generator reaches the detector. In one embodiment, the read out rate of such an individual pixel may be fabricated to be read out at about one hundred times the frame read out rate. The detector may be programmed to monitor this individual photosensor to detect a start time of the x-ray generator. In one embodiment, the special individual photosensor may be fabricated as a photodiode connected separately to the read out circuitry disclosed herein for detecting x-ray pulses from the x-ray generator. In one embodiment, the detector uses the determined start time of the generator emitting the detected x-ray pulse to synchronize its internal clock and thereby schedule and control its integration periods. In one embodiment, the x-ray generator may be controlled by the image processing system 34 to emit an x-ray pulse during the detector's first mode of operation at a lower energy or at a shorter duration, or both, than the pulses it emits during the second mode wherein typical radiographic examination energy levels and durations are used. Thereby, a patient is exposed to lower x-ray energy during a synchronization pulse procedure undertaken by the x-ray generator and the x-ray detector. The specialized photosensor disclosed herein, or a different photosensor, may be continuously monitored by the image processing system 34 to maintain detector synchronization or to detect synchronization drift during an imaging exam.

In one embodiment, an x-ray system may be synchronized as described herein, without first communicating a frame rate to the x-ray generator 14 and the detector 40. The detector may be programmed to operate in a first mode whereby the detector monitors one or more selected pixels of the detector to detect x-ray pulses from the x-ray generator. A start time of a first pulse 603 detected by the detector, using means described herein, is recorded in the detector relative to an internal clock of the detector. A start time of a second pulse 605, is detected by the detector, using means described herein, and the frame rate 604 is calculated based on the duration between the first two pulses 603, 605. Thus, the detector calculates a start time of the next x-ray pulse based on the calculated frame rate and recoded start times of the first two pulses 603, 605. The detector thereby adjusts its integration periods in a second mode of normal imaging operation to synchronize with the x-ray pulses (FIG. 6) as described herein. The pulses 603, 605, may be of a lower energy or shorter duration, or both, compared to regular patient imaging energies and durations.

It will be appreciated that the methods described herein are performed by an appropriately programmed x-ray image processing system 10, 500. As disclosed herein, an x-ray imaging system may include a wireless flat or curved panel digital radiographic detector 40 having an internal clock and programmed to controllably schedule its integration periods. An x-ray generator 14 is included and is configured to controllably fire x-ray pulses at a preset frame rate. Both the detector 40 and the x-ray generator 14 are communicatively coupled to an image processing system 34 wirelessly (the detector) and by hard wire (the x-ray generator) to receive a frame rate transmitted from the image processing system 34. The detector 40 is programmed, or configured, to monitor one or more selected pixels in the detector array to detect an x-ray pulse emitted from the x-ray generator 14 and to determine a start time of the detected x-ray pulse according to the internal clock. The detector is further configured to controllably schedule, or synchronize, integration periods of the detector with start times of the generator emitting x-ray pulses based on the communicated frame rate and the determined start time of the detected x-ray pulses.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method for synchronizing operation between a digital radiographic detector's integration periods and an x-ray generator's x-ray pulse rate, the method comprising:
   communicating the x-ray generator's x-ray pulse rate to the detector;
   the detector monitoring one or more selected pixels in the detector to detect an x-ray pulse emitted from the x-ray generator;
   the detector detecting the x-ray pulse emitted from the x-ray generator and determining a start time at which the x-ray generator emitted the detected x-ray pulse relative to an internal clock of the detector; and
   the detector adjusting a timing of the detector's integration periods to synchronize with the x-ray generator's x-ray pulse rate based on the communicated x-ray generator's x-ray pulse rate and the determined start time at which the x-ray generator emitted the detected x-ray pulse.

2. The method of claim 1, further comprising monitoring, at a rate at least about 10× a row read out rate of the detector, one selected pixel in the detector to detect the x-ray pulse emitted from the x-ray generator.

3. The method of claim 1, further comprising monitoring an embedded photodiode in the detector, at a rate at least about 100× a frame read out rate of the detector, to detect the x-ray pulse emitted from the x-ray generator.

4. The method of claim 1, further comprising the x-ray generator emitting the detected x-ray pulse at a lower energy or at a shorter duration than x-ray pulses emitted subsequently.

5. The method of claim 1, further comprising monitoring a sensor in the detector to detect synchronization drift, if any.

6. The method of claim 1, further comprising communicating the x-ray generator's x-ray pulse rate in microseconds to the detector, wherein the x-ray generator's x-ray pulse rate comprises a time duration between x-ray pulses.

7. The method of claim 1, further comprising operating the detector in a first mode by reading out one or more frames from the detector row by row continuously.

8. The method of claim 7, further comprising the detector monitoring each read out row to detect during which row being read out the detected x-ray pulse emitted from the x-ray generator reaches the detector.

9. The method of claim 8, further comprising the detector determining the start time at which the generator emitted the detected x-ray pulse relative to the internal clock of the detector using a known row read out time interval corresponding to the detector and a row number of the row being read out when the detected x-ray pulse reached the detector.

10. The method of claim 1, wherein the step of communicating the x-ray generator's x-ray pulse rate is performed wirelessly under control of an x-ray processing system.

11. The method of claim 1, further comprising monitoring a specialized individual photosensor in a photosensor array of the detector at a read out rate at least about 10× a row read out rate of the detector to detect when an x-ray pulse from the x-ray generator reaches the detector.

12. The method of claim 1, further comprising storing the determined start time at which the x-ray generator emitted the detected x-ray pulse relative to a readout start time for a first row of pixels in the detector.

13. The method of claim 1, further comprising calculating a difference in start times as between the determined start time at which the x-ray generator emitted the detected x-ray pulse and a start time of reading out a selected row, and selectively synchronizing subsequent times of reading out the selected row to coincide with the subsequent times of the generator emitting x-ray pulses.

14. An x-ray imaging system comprising:
  a wireless digital radiographic detector comprising an internal clock and configured to controllably adjust a timing of the detector's integration periods;
  an x-ray generator configured to controllably fire a series of x-ray pulses at a preset frame rate; and
  a processing system coupled to the detector and coupled to the x-ray generator to communicate the preset frame rate to the detector and the generator,
  wherein the detector is configured to monitor one or more selected pixels in the detector to detect the series of x-ray pulses from the x-ray generator and to determine a start time of the detected series of x-ray pulses relative to the internal clock,
  and wherein the detector is configured to controllably adjust the timing of the detector's integration periods to synchronize with the series of x-ray pulses from the x-ray generator based on the communicated frame rate and the determined start time of the detected series of x-ray pulses.

15. The system of claim 14, further comprising an embedded photodiode in the detector to detect the series of x-ray pulses from the x-ray generator.

16. A method for synchronizing a digital radiographic detector's integration periods with an x-ray generator's x-ray pulse rate, the method comprising:
  the detector detecting a first x-ray pulse emitted from the x-ray generator and determining a start time of the x-ray generator emitting the detected first x-ray pulse relative to an internal clock of the detector;
  the detector detecting a second x-ray pulse from the x-ray generator relative to the internal clock of the detector and, in response to the steps of detecting the first and second x-ray pulses, determining the x-ray generator's x-ray pulse rate; and
  the detector selectively adjusting integration periods of the detector to synchronize with the x-ray generator's x-ray pulse rate based on the determined x-ray generator's x-ray pulse rate and the determined start time of the x-ray generator emitting the detected first x-ray pulse.

17. The method of claim 16, further comprising monitoring an embedded photodiode in the detector to detect the first x-ray pulse emitted from the x-ray generator.

18. An x-ray imaging system comprising:
  a wireless digital radiographic detector comprising an internal clock and configured to schedule integration periods at selected times;
  an x-ray generator configured to fire x-ray pulses at a preset frame rate; and
  wherein the detector is configured to monitor one or more selected pixels in the detector to detect the x-ray pulses fired by the x-ray generator, to determine a start time of the x-ray pulses fired by the x-ray generator relative to the internal clock, to determine the preset frame rate based on only two of the detected x-ray pulses, and to selectively initiate the integration periods of the detector to be synchronized with the x-ray pulses fired by the x-ray generator based on the determined start time of the x-ray pulses and the determined preset frame rate.

19. The x-ray imaging system of claim 18, further comprising a photodiode in the detector to detect the x-ray pulses fired by the x-ray generator.

* * * * *